United States Patent [19]

Ya

[11] Patent Number: 5,059,178

[45] Date of Patent: Oct. 22, 1991

[54] METHOD OF PERCUTANEOUSLY REMOVING A THROMBUS FROM A BLOOD VESSEL BY USING CATHETERS AND SYSTEM FOR REMOVING A THROMBUS FROM A BLOOD VESSEL BY USING CATHETERS

[76] Inventor: Wang D. Ya, Qian Fo Shan Lu 3 Hao, Ji Nan Shi, Shan Dong Sheng, China

[21] Appl. No.: 298,547

[22] Filed: Jan. 18, 1991

[30] Foreign Application Priority Data

Aug. 3, 1988 [JP] Japan .............................. 63-194133

[51] Int. Cl.⁵ .............................................. A61M 25/02
[52] U.S. Cl. .................................... 604/101; 604/96
[58] Field of Search .................. 604/53, 96, 101, 102, 604/103, 104; 606/159, 191, 192, 194

[56] References Cited

U.S. PATENT DOCUMENTS

| | | | |
|---|---|---|---|
| 4,445,892 | 5/1984 | Hussein et al. | 604/101 |
| 4,573,470 | 3/1986 | Samson et al. | 604/96 |
| 4,573,966 | 3/1986 | Weikl et al. | 604/101 |
| 4,610,662 | 9/1986 | Weikl et al. | 604/101 |
| 4,636,195 | 1/1987 | Wolinsky | 604/101 |
| 4,723,549 | 2/1988 | Wholey et al. | 604/101 |
| 4,824,436 | 4/1989 | Wolinsky | 604/53 |
| 4,832,028 | 5/1989 | Patel | 604/101 |
| 4,909,252 | 3/1990 | Goldberger | 604/96 |
| 4,911,163 | 3/1990 | Fina | 604/101 |
| 4,921,478 | 5/1990 | Solano et al. | 604/96 |
| 4,930,496 | 6/1990 | Bosley, Jr. | 604/101 |

FOREIGN PATENT DOCUMENTS 627828  10/1978  U.S.S.R. .............................. 604/101

Primary Examiner—Stephen C. Pellegrino
Assistant Examiner—Ralph A. Lewis
Attorney, Agent, or Firm—Edwin E. Greigg; Ronald E. Greigg

[57] ABSTRACT

A method of percutaneously removing a thrombus from a blood vessel by using catheters and thrombus removing system for executing the method. A guide wire catheter includes a first balloon inflatable for blocking the blood vessel at a position downstream of the thrombus. A suction catheter includes a second balloon inflatable for substantially blocking the blood vessel at a position upstream of the thrombus. A thrombus dissolving agent is supplied to a position between the first and second balloons, and dissolved thrombus is drawn through the suction catheter out of the body. An expansion catheter having a third balloon is used to expand, while allowing blood flows, a location of stricture remaining after removal of the dissolved thrombus.

1 Claim, 6 Drawing Sheets

METHOD OF PERCUTANEOUSLY REMOVING A THROMBUS FROM A BLOOD VESSEL BY USING CATHETERS AND SYSTEM FOR REMOVING A THROMBUS FROM A BLOOD VESSEL BY USING CATHETERS

BACKGROUND OF THE INVENTION

1. Field of the Invention

The present invention relates to a method of percutaneously removing a thrombus from an artery or a vein in various parts of the body by using catheters, and a system for removing a thrombus from a blood vessel by using catheters. More particularly, the invention relates to a method and a system for percutaneously removing a thrombus from a blood vessel by using catheters, which method and system are well suited for removing a thrombus from a coronary artery in particular.

2. Description of the Prior Art

There are various causes for acute myocardial infarction, and one of the known causes is blocking of a coronary artery by a thrombus. Techniques employed heretofore to treat this type of blocking by a thrombus are classified broadly into the following three methods:

(a) A surgical, bypassing operation for the location of thrombosis, (b) Percutaneous Transluminal Coronary Recanalization (known as PTCR), and (c) Percutaneous Transluminal Coronary Angioplasty (known as PTCA).

The surgical operation above is a major operation involving chest incision and running considerable risks. It resorts to bypassing and not removal of the thrombus per se. Such an operation is seldom carried out since it is costly.

PTCR is a method in which a thrombus dissolving agent is injected to the location of thrombosis in a coronary artery by using catheters. This method has the following problems:

1. Although PTCR may succeed in resuming blood flow, the thrombus is not completely dissolved. Consequently, stenotic lesion remains in a serious degree, which may cause post-infarction angina pectoris and re-blocking.

2. Where a large quantity of thrombus dissolving agent is used in order to completely dissolve and remove the thrombus, the dissolving agent is injected from a catheter to a position adjacent the location of thrombosis and becomes diluted by blood before the dissolving agent reaches the location of thrombosis. If the quantity of thrombus dissolving agent is increased to anticipate the dilution, not only hemorrhage will occur at other locations than the heart but there are many cases of hemorrhage occurring at the location of myocardial infarction with blood flow resumption, namely hemorrhagic infarction.

PTCA is a method of pressurizing and expanding a location of coronary artery blockage from inside by inflating a balloon attached to a catheter.

Since, in the state of the art, PTCA leaves the thrombus as it is instead of removing it, there is a problem of re-blocking taking place immediately following or several months after the treatment. This method has a further problem that the thrombus broken up through pressurization and expansion of the thrombotic location may block peripheral blood vessels, thereby causing a circulatory disorder.

SUMMARY OF THE INVENTION

A primary object of the present invention is to provide a novel method of percutaneously removing a thrombus from a blood vessel by using catheters, and a novel system for removing a thrombus from a blood vessel by using catheters, which method and system solve the problems of the prior art noted above, allow a treatment (or an operation) to be carried out at low cost, assures a high degree of post-operative safety, and is capable of almost completely removing a thrombus blocking an artery or a vein (especially a coronary artery), thereby realizing an excellent treatment with hardly any possibility of re-blocking or hemorrhage at various locations (including parts other than the heart).

In order to achieve the above object, a method of percutaneously removing a thrombus from a blood vessel by using catheters, according to the present invention, comprises the steps of inflating a first balloon included in a guide wire catheter for blocking the blood vessel at a position adjacent and downstream of the thrombus, inflating a second balloon included in a balloon catheter for substantially blocking the blood vessel at a position upstream of the thrombus, supplying a thrombus dissolving agent to a position between the first and second balloons for dissolving the thrombus, and drawing the dissolved thrombus out of the body.

The term "substantially blocking the blood vessel" used above includes both complete blocking of the blood vessel and blocking with an allowance for slight blood flow.

Further, a thrombus removing system using catheters, according to the present invention, comprises a guide wire catheter including a hollow main body, a guide wire extending from a forward end of the main body, and a first balloon disposed adjacent the forward end for blocking a blood vessel, the first balloon being inflatable under a predetermined internal pressure and deflatable under a pressure less than the predetermined internal pressure, the main body defining a supply opening for supplying liquid to inflate the first balloon, and outflow bores located at upstream positions of the main body with respect to a direction of blood flow for supplying a thrombus dissolving agent; a thrombus suction catheter having a hollow construction for receiving the guide wire catheter, and including a suction passage for collecting the thrombus as dissolved and the thrombus dissolving agent, and a second balloon disposed adjacent a forward end thereof, the second balloon being formed against inward and outward overexpansion under a predetermined pressure, the thrombus suction catheter defining a supply passage for supplying liquid to inflate the second balloon; means for supplying the liquid under pressure to inflate the first balloon; means for supplying the thrombus dissolving agent under pressure; means for supplying the liquid under pressure to inflate the second balloon; and suction means for collecting the thrombus as dissolved and the thrombus dissolving agent.

The means for supplying the liquid under pressure to inflate the first balloon, as included in the above system, acts also as the means for supplying the thrombus dissolving agent under pressure where the thrombus dissolving agent is used as the balloon inflating liquid (which usually is the case).

In a preferred embodiment of the invention, the liquid supply passage is defined by an outer tube of the thrombus suction catheter having a double tube construction, and the suction passage comprises a space in the thrombus suction catheter remaining after the guide wire catheter is inserted thereinto.

How the method and system for percutaneously removing a thrombus from a blood vessel by using catheters according to the present invention will be described now. The first balloon blocks a blood vessel at a position downstream of a thrombus and the second balloon substantially blocks the blood vessel at a position upstream of the thrombus when their internal pressures reach a predetermined level. A thrombus dissolving agent is directly injected to the thrombus in the substantially sealed part of the blood vessel between the two balloons, thereby to dissolve the thrombus. Thus, the dissolving agent produces excellent thrombus dissolving results without being diluted by blood, as distinct from the prior art in which the dissolving agent is injected to a position spaced from a thrombus. Further, since the dissolved thrombus and the dissolving agent are removed outside the body, the dissolving agent may be used in a large quantity without possibility of its flowing forward or backward through the blood vessel to cause hemorrhage in other parts of the body, and there is no possibility of the dissolved thrombus flowing away to block other blood vessels. This feature promotes the safety of a surgical operation to remove a thrombus.

The fact that the thrombus dissolving agent is substantially completely prevented from flowing to other parts of the body, allows the dissolving agent to have a relatively high concentration for application to the thrombus per se, to assure reliable dissolution of the thrombus.

The thrombus removing system according to the present invention may further comprise an expansion catheter for expanding a location of stricture after removal of the thrombus. This expansion catheter is effective, when there should remain small fractions of the thrombus in the blood vessel, to assure resumption of blood flow through the blood vessel, e.g. a coronary artery.

The guide wire catheter and thrombus suction catheter are used in treatments, involving only inflation and deflation of the first and second balloons. The thrombus removing method and system according to the present invention require no special drive or other complicated mechanisms to sever a thrombus. Thus the catheters of the present invention are capable of highly reliable operation with hardly any possibility of breakdown or malfunction.

When the present invention is used for a coronary artery, the catheters are normally inserted from a right or left artery through the aorta into the coronary artery as in the conventional PTCA. Thus the invention avoids such great risks as run by a surgical operation involving chest incision.

Other objects, features and advantages of the present invention will be apparent from the following description.

BRIEF DESCRIPTION OF THE DRAWINGS

The drawings illustrate a method and a system for percutaneously removing a thrombus from a blood vessel by using catheters according to the present invention, in which.

DESCRIPTION OF THE PREFERRED EMBODIMENT

A method of percutaneously removing a thrombus from a blood vessel by using catheters according to the present invention, and a thrombus removing system for executing this method to suit the treatment of thrombotic blocking of a coronary artery will be described hereinafter with reference to the drawings. The following description gives work dimensions with certain ranges. This is because, in practice, several types are manufactured to permit selection of the best suited device for a particular location of thrombotic blocking in the coronary artery.

Figure 1:
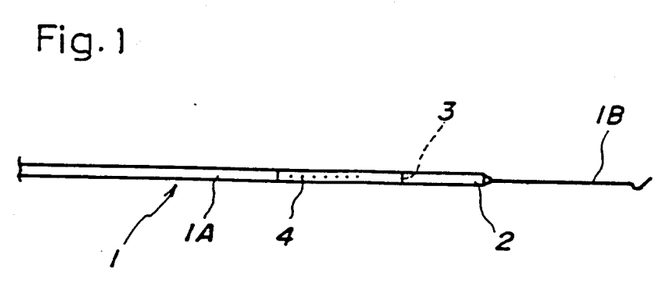
FIG. 1 is a side view, partly broken away, of a guide wire catheter with a first balloon uninflated.
Figure 2:
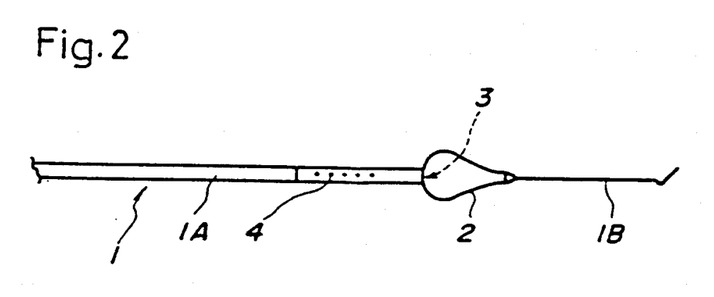
FIG. 2 is a side view, partly broken away, of the guide wire catheter with the first balloon inflated.

Referring to FIGS. 1 and 2, a guide wire catheter 1 comprises a hollow main body 1A and a guide wire 1B attached to a forward end of the main body 1A.

As does a conventional guide wire, the guide wire 1B has a distal end curved in a special way for acting as a guide to pass through a branching position of a blood vessel. The guide wire 1B may be formed of the same metal or special plastic as used for the guide wire employed in PTCA as long as the material, desirably, has a smooth surface and is flexible. This guide wire 1B is 3 cm long and 0.012 inches in shaft diameter, although the suitable ranges are 2–10 cm and 0.012–0.018 inches, respectively. The hollow main body 1A is formed of an appropriate plastic such as polyethylene, which may be combined with a metal wire to prevent breakage and expansion under pressure. The main body 1A is 160 cm long, 0.5 mm in inside diameter and 0.7 mm in outside diameter, although the suitable ranges are 135-180 cm, 0.3-0.8 mm and 0.5-1.0 mm, respectively.

The main body 1A carries a first balloon 2 for blood vessel blocking attached to the forward end thereof. The main body 1A also defines a supply opening 3 for supplying liquid (which is a thrombus dissolving agent alone or in combination with a diluted contrast medium) to inflate the first balloon 2, and a plurality of dissolving agent outflow bores 4. The forward end of the main body 1A has a plurality of metallic marks (not shown) for fluoroscopy.

The first balloon 2 has a tubular shape and attached to extend continuously from the forward end of the main body 1A. The first balloon 2 is 7 mm long and 0.8 mm in outside diameter in an uninflated state, although the suitable ranges are 2-10 mm and 0.5-1.2 mm, respectively. The first balloon 2 is inflatable to a size sufficient to block a blood vessel, e.g. to a diameter of several millimeters.

The first balloon 2 is formed of a very thin, elastic material such as rubber or plastic. It begins to inflate under pressure, e.g. under 3 atm. (FIG. 2 shows the inflated balloon), and automatically deflates under a pressure less than 3 atm. (FIG. 1). The first balloon 2 in the deflated state maintains the guide wire 1B substantially horizontal, and has a sufficient stiffness to advance against resistance through a blood vessel. The supply opening 3 is defined in the forward end of the main body 1A for inflating the first balloon 2, which opening 3 is located inside the first balloon 2.

The thrombus dissolving agent outflow bores 4 comprise fine bores which provide a maximum discharge up to, for example, 3 atm. (the discharge does not increase with an increase of the pressure over 3 atm.). It is preferable to provide several such bores, but one may serve the purpose. The bores have a distribution range which is spaced 1.5 cm from adjacent the balloon, though it may be spaced 1-2 cm therefrom, and extends over a length of 2 cm along the main body 1A, though it may extend over a length of 1-4 cm. The maximum discharge through the bores is determined by an amount of the thrombus dissolving agent. In other words, the size of the fine bores is determined by the maximum discharge. For example, where the maximum discharge is 5 cc per minute, the size of the fine bores may be determined by the 5 cc per minute.

The thrombus dissolving agent used here may be the same as the agent used in the conventional PTCR.

FIGS. 2 through 7 show a suction catheter 5, for drawing a thrombus, which comprises a hollow main body 1A for receiving the main body 1A of the guide wire catheter 1, a suction passage 6 is disposed in the main body 5A for collecting a dissolved thrombus and the thrombus dissolving agent, a second balloon 7 is provided adjacent a forward end of the main body 5A, and a supply passage 8 is provided for supplying liquid to inflate the second balloon 7.

Figure 3:
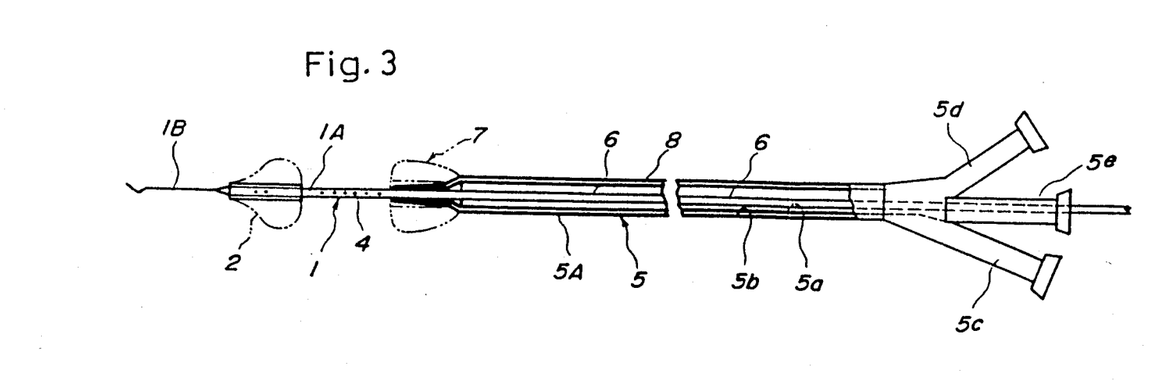
FIG. 3 is a side view, partly broken away, of a suction catheter.

The main body 5A of the suction catheter 5 is formed of polyethylene as is the main body 1A, and defines trident connectors 5c, 5d and 5e at a proximal end thereof (which is disposed outside the patient's body). The main body 5A is 100 cm long, 2 mm in outside diameter and 2 mm in inside diameter, although the suitable ranges are 100-110 cm, 1.5-3.0 mm and 1.0-2.5 mm, respectively.

Figure 4:
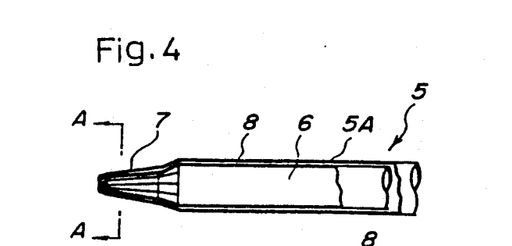
FIG. 4 is an enlarged side view, partly broken away, of a principal portion of the suction catheter with a second balloon uninflated.

The second balloon 7 has a soft, funnel-shaped, tapering forward end which defines an opening having a 1.5 mm inside diameter, though its suitable range is 0.5-2.5 mm. The second balloon 7 is 2 cm though its suitable range is 0.5-3.0 cm. The second balloon 7, which is in bag-like form, includes very thin inner and outer films of polyethylene terephthalate, polyolefine or the like which does not undergo inward or outward overexpansion when a certain fixed pressure is applied thereto.

Figure 5:
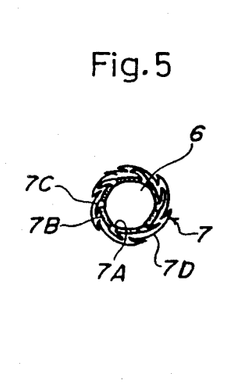
FIG. 5 is a section taken on line A—A of FIG. 4.

The tapered portion of the second balloon 7 has an inside wall including elastic webs 7A and relatively rigid wall parts 7B alternately arranged and interconnected in the peripheral direction. The inside wall is surrounded by an inelastic film 7C extending so as to interconnected the rigid wall parts 7B, to define a bag-like construction together. An outermost wall 7D is disposed outwardly of the inelastic film 7C defining an expansion space therebetween. Thus, the second balloon 7 has a triplex construction.

Figure 6:
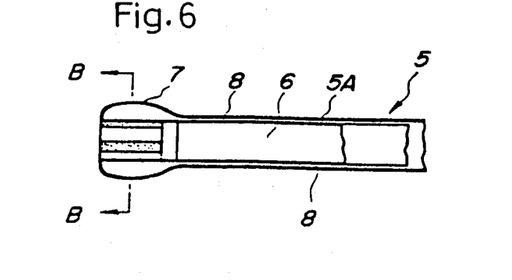
FIG. 6 is an enlarged side view, partly broken away, of the principal portion of the suction catheter with the second balloon inflated.
Figure 7:
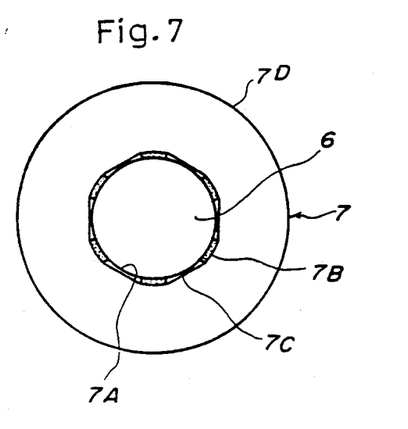
FIG. 7 is a section taken on line B—B of FIG. 6.

When inflating liquid is injected under pressure into the second balloon 7, the forward end thereof becomes inflated with extension of the webs 7A, thereby enlarging the inside diameter thereof as shown in FIG. 6. At this time, the inside diameter of the forward end equals the inside diameter of the main body 5A, to facilitate suction of the dissolved thrombus and the dissolving agent, with the outside diameter enlarged to block the blood vessel.

The enlarged diameter of the second balloon 7 is 3.0 mm though its suitable range is 2.0-5.0 mm. With a reduction in the liquid pressure, the forward end of the second balloon 7 returns to the original, funnel shape due to the elastic restoring force of the innermost webs (of rubber) 7A. In this original position, the outermost wall 7D is folded up into pleats as shown in FIG. 5.

The main body 5A has a double tube construction comprising an inner tube 5a and an outer tube 5b, and the supply passage 8 is defined between the two tubes 5a and 5b for supplying the liquid to inflate the second balloon 7. The outer tube 5b is connected to one of the trident connectors 5c, whereas the inner tube 5a is connected to the other connectors 5d and 5e.

The suction passage 6 is defined in the inner tube 5a for collecting the dissolved thrombus and the thrombus dissolving agent. As described hereinbefore, the guide wire catheter 1 is inserted into the inner tube 5a. Thus, what is left of the sectional area of the inner tube 5a after subtracting that of the guide wire catheter 1 is available to act as the suction passage 6.

Figure 8:
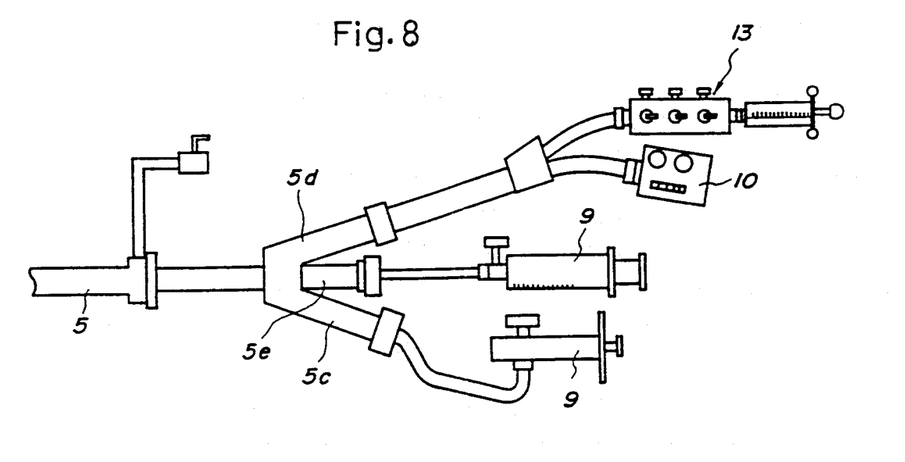
FIG. 8 is a side view of injectors.
Figure 9:
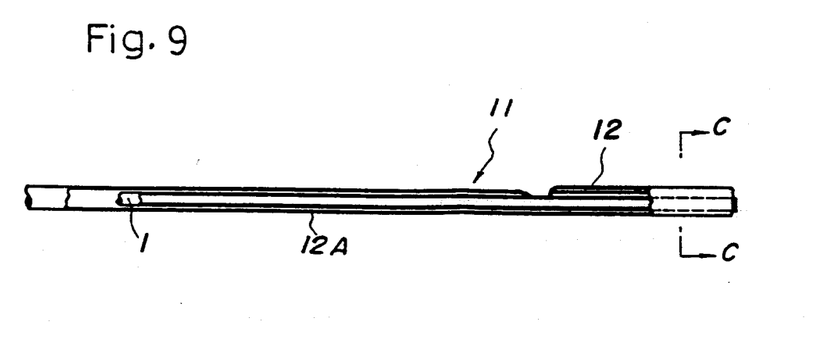
FIG. 9 is a side view, partly broken away, of an expansion catheter in an uninflated state.
Figure 10:
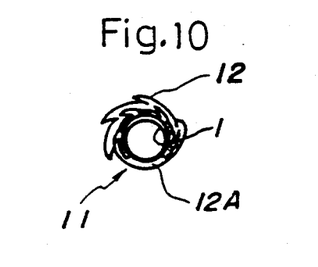
FIG. 10 is a section taken on line C—C of FIG. 9.
Figure 11:
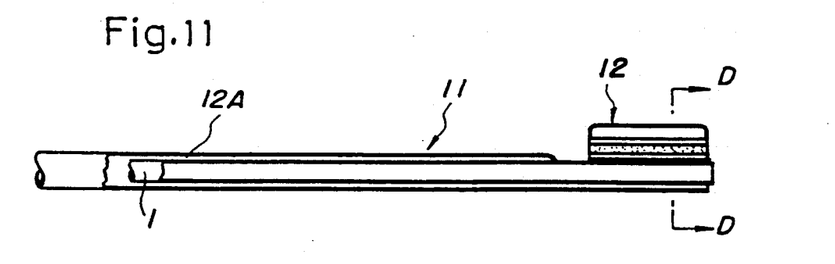
FIG. 11 is a side view, partly broken away, of the expansion catheter in an inflated state.
Figure 12:
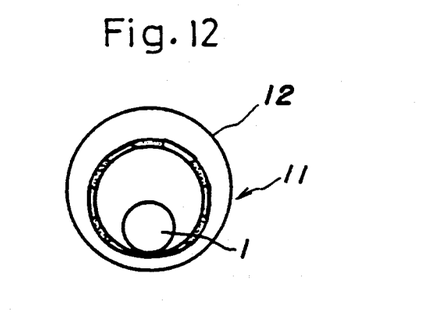
FIG. 12 is a section taken on line D—D of FIG. 11.
Figure 13:
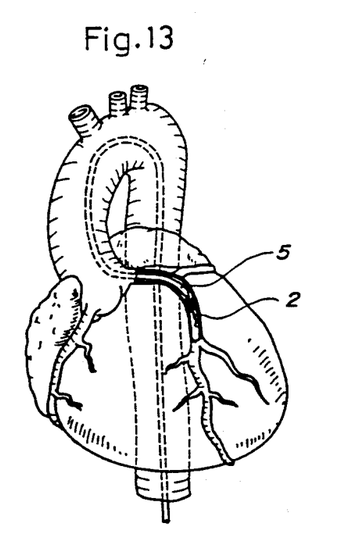
FIG. 13 is a perspective view, partly broken away, of a heart to which the present invention is applied.

FIG. 8 shows a liquid injector 9, which itself is known, for producing a pressure exceeding 3 atm. to inflate the first balloon 2. Thus, its detailed description is omitted here.

Means for injecting the thrombus dissolving agent and inflating the first balloon 2 also comprises the known injector 9 as shown in FIG. 8.

Reference number 10 indicates a known electric suction device which acts as a suction pump. This device 10 produces a negative pressure to collect the dissolved thrombus and the thrombus dissolving agent.

The injector 9 may comprise a pump controlled by an electric motor, and a valve which is also electrically controlled. The suction device 10 may also comprise a mechanical pump.

Reference number 13 in FIG. 8 indicates a contrast medium injector.

FIGS. 9 through 12 show an expansion catheter 11 used for expanding a location of stricture remaining after the thrombus removing treatment according to the present invention.

The expansion catheter 11 has a hollow construction for receiving the guide wire catheter 1, and includes a third balloon 12 at a forward end thereof. The third balloon 12 is substantially in the form of hollow cylinder inside to be inflatable while allowing blood flows. A supply passage 12A is defined by a double tube construction, for supplying a balloon inflating liquid. The expansion catheter 11 is used as fitted on the guide wire catheter 1 after removal of the thrombus. The third balloon 12 is formed of the same material as the webs 7A of the second balloon 7.

Next, a sequence of operation with the system according to the present invention will be described with reference to FIGS. 13 through 16.

Figure 14:
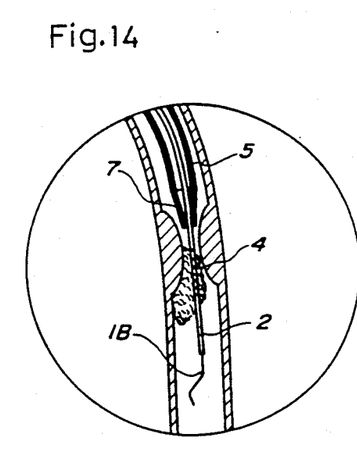
FIG. 14 is an enlarged view in vertical section of a principal part into which the guide wire catheter is inserted.
Figure 15:
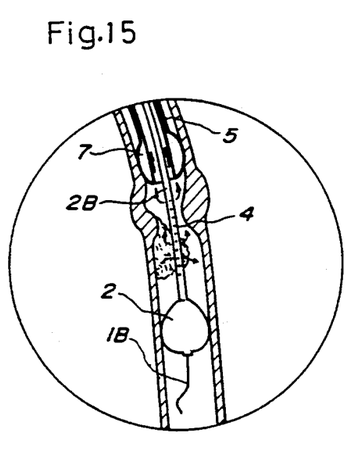
FIG. 15 is an enlarged view in vertical section of the principal part into which a thrombus dissolving agent is injected.
Figure 16:
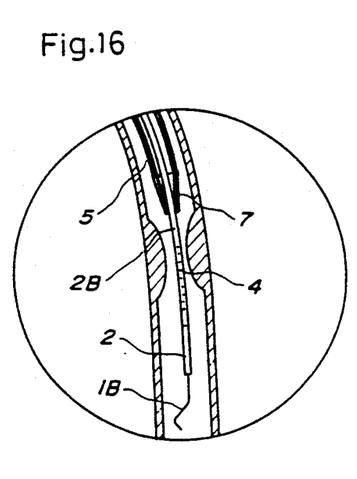
FIG. 16 is an enlarged view in vertical section of the principal part from which a thrombus has been removed.

A sheath is first inserted into and fixed in the right or left artery. Then a short guide wire is inserted through the sheath, and thereafter the sheath is withdrawn. Next, a valved artery sheath is inserted along the guide wire. Then a guide catheter is inserted as far as the inlet of the coronary artery. Thereafter, as shown in FIG. 14, the guide wire catheter 1 of the present invention is inserted through the guide catheter, penetrating a thrombus in the coronary artery. The guide catheter is then withdrawn. Next, the suction catheter 5 is inserted along the guide wire catheter 1 to a position just short of the thrombus. The second balloon 7 of the suction catheter 5 is first inflated, and then the first balloon 2 of the guide wire catheter 1 is inflated. The first and second balloons 2 and 7 are inflated by injecting the thrombus dissolving agent from the injector 9 shown in FIG. 8. The thrombus is dissolved by the injected dissolving agent as shown in FIG. 15. The dissolved thrombus is drawn through the suction catheter 5 out of the body. This treatment is observed on an X-ray monitor (FIG. 16), which is made possible by the contrast medium injected from the injector 14 (FIG. 8) through the suction catheter 5. After the treatment, the guide wire catheter 1 is withdrawn first and then the suction catheter 5 is withdrawn.

Modifications of the components used in the system according to the present invention will be described next.

1. Guide Wire Catheter 1'

Figure 17:
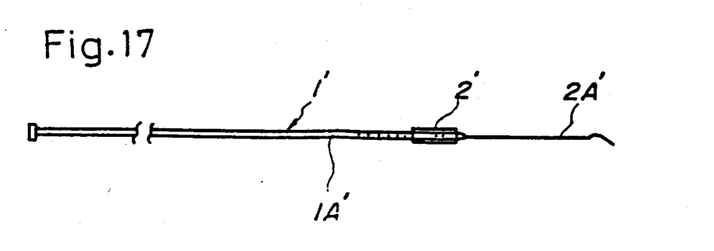
FIG. 17 is a side view of a modified guide wire catheter with a first balloon uninflated.
Figure 18:
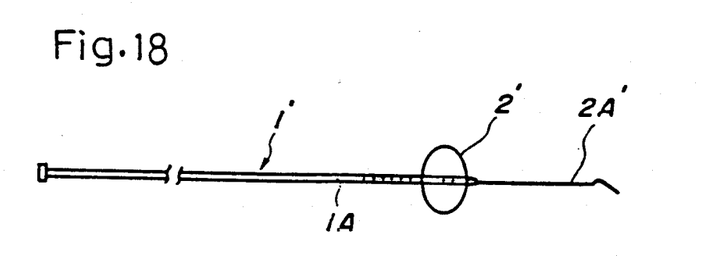
FIG. 18 is a side view of the guide wire catheter of FIG. 17 with the first balloon inflated.

This guide wire catheter 1' is different from the foregoing guide wire catheter 1 in the construction of the main body. As shown in FIGS. 17 and 18, the modified main body 1A' is divided by a radial partition. One of the passages formed by the partition wall is used for supplying the thrombus dissolving agent to inflate a first balloon 2', and the other passage is used for supplying the thrombus dissolving agent directly to a thrombus.

The first balloon 2' preferably is formed of rubber film where the main body 1A' is about 1.0 mm in diameter.

Figure 19:
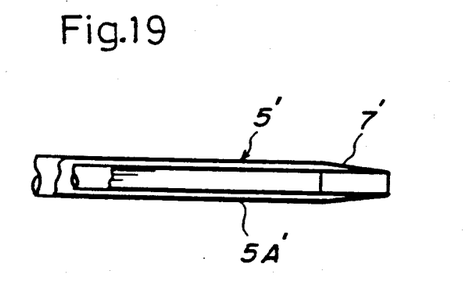
FIG. 19 is a side view of a modified suction catheter with a second balloon uniflated.
Figure 20:
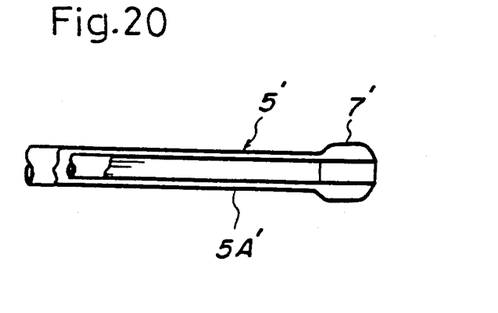
FIG. 20 is a side view of the suction catheter of FIG. 19 with the second balloon inflated.
Figure 21:
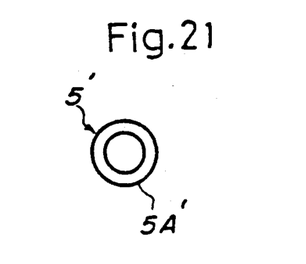
FIG. 21 is a section taken on line E—E of FIG. 20.

2. Suction Catheter 5'

Where the suction catheter is used adjacent the inlet of a coronary artery, the suction catheter need not include a tapered forward end. Thus, as shown in FIGS. 19 through 21, and as distinct from the forgoing suction catheter 5, the modified suction catheter 5' has a forward end having approximately the same diameter as a main body 5'. A second balloon 7' provided at the forward end is formed of thin rubber.

What is claimed is:

1. A thrombus removing system using catheters, comprising:

a guide wire catheter, said guide wire catheter including a hollow main body including a rear end and a forward end, a guide wire extending from the forward end of the hollow main body, and a first balloon disposed adjacent the forward end of said hollow main body for blocking blood flow in a blood vessel, the first balloon being inflatable under a predetermined internal pressure and deflatable under a pressure less than the predetermined internal pressure, the hollow main body defining a supply opening for supplying a first fluid to inflate the first balloon, and outflow bores in said hollow main body located at a position rearward of said first balloon for supplying a thrombus dissolving agent to a rear area of said first balloon, a thrombus suction catheter having a hollow construction for receiving the guide wire catheter, and including a suction passage for collecting the thrombus as dissolved and the thrombus dissolving agent, and a second balloon disposed adjacent a forward end of said thrombus suction catheter toward the rear of said hollow main body from said outflow bores with said forward end of said guide wire catheter extending beyond the forward end of said thrombus suction catheter, the second balloon being formed against inward and outward overexpansion under a predetermined pressure, the second balloon including an inside wall comprised of elastic webs and relatively rigid wall parts alternately arranged and interconnected in the peripheral direction, said inside wall being surrounded by an inelastic film extending so as to interconnect the rigid wall parts to define a substantially bag-like construction together, and further including an outermost wall disposed outwardly of the inelastic film so as to define an expansion space therebetween, the thrombus suction catheter defining a second fluid supply passage for supplying a second fluid to inflate the second balloon, said second fluid supply passage being further defined by an outer tube of the thrombus suction catheter having a double tube construction, and the suction passage comprising a space in the thrombus suction catheter between the guide wire catheter and the thrombus suction catheter remaining after the guide wire catheter is inserted thereinto, means for supplying the first fluid under pressure to inflate the first balloon, means for supplying the thrombus dissolving agent under pressure, means for supplying the second fluid under pressure to inflate the second balloon, and suction means for collecting the thrombus as dissolved and the thrombus dissolving agent.

* * * * *

UNITED STATES PATENT AND TRADEMARK OFFICE
CERTIFICATE OF CORRECTION

PATENT NO. : 5,059,178
DATED : October 22, 1991
INVENTOR(S) : Ya Dong Wang

It is certified that error appears in the above-identified patent and that said Letters Patent is hereby corrected as shown below:

On the title page, items [19] and [76]
The inventor's name should read as follows:

[76] Inventor: Ya Dong Wang, Qian Fo Shan Lu 3 Hao, Ji Nan Shi, Shan Dong Sheng, CHINA Signed and Sealed this Ninth Day of March, 1993

*Attest:*

STEPHEN G. KUNIN

*Attesting Officer*      *Acting Commissioner of Patents and Trademarks*